United States Patent
Bryson et al.

(10) Patent No.: US 9,538,762 B2
(45) Date of Patent: Jan. 10, 2017

(54) ANTIMICROBIAL DELIVERY SYSTEM FOR ROOF COVERINGS

(75) Inventors: Michael L. Bryson, Independence, MO (US); Paul G. Wilson, Waxahachie, TX (US); Matti Kiik, Richardson, TX (US); Phillip Kleinlauth, Ovilla, TX (US)

(73) Assignee: Building Materials Investment Corporation, Wilmington, DE (US)

( * ) Notice: Subject to any disclaimer, the term of this patent is extended or adjusted under 35 U.S.C. 154(b) by 108 days.

(21) Appl. No.: 12/651,350

(22) Filed: Dec. 31, 2009

(65) Prior Publication Data

US 2011/0159237 A1 Jun. 30, 2011

(51) Int. Cl.
*A01N 59/16* (2006.01)
*A01N 59/20* (2006.01)
*E04D 13/00* (2006.01)
*E04D 1/22* (2006.01)

(52) U.S. Cl.
CPC ............... *A01N 59/16* (2013.01); *A01N 59/20* (2013.01); *E04D 1/22* (2013.01); *E04D 13/002* (2013.01); *Y10T 156/10* (2015.01); *Y10T 428/24355* (2015.01)

(58) Field of Classification Search
CPC ....... A01N 59/16; A01N 59/20; E04D 13/002; Y10T 156/10; Y10T 428/24355
USPC ................................. 428/141–150
See application file for complete search history.

(56) References Cited

U.S. PATENT DOCUMENTS

| | | | |
|---|---|---|---|
| 5,356,664 A * | 10/1994 | Narayan et al. ............... | 427/186 |
| 6,420,455 B1 * | 7/2002 | Landgrebe et al. .......... | 523/122 |
| 6,936,644 B2 * | 8/2005 | Gilleo ........................... | 523/205 |
| 7,354,596 B1 * | 4/2008 | Banovetz et al. ............ | 424/408 |
| 2001/0016626 A1 * | 8/2001 | Vollenberg et al. .......... | 525/165 |
| 2005/0136216 A1 * | 6/2005 | Koschitzky ................... | 428/141 |
| 2007/0148342 A1 * | 6/2007 | Kalkanoglu et al. ......... | 427/212 |
| 2007/0213299 A1 * | 9/2007 | Klein et al. .................... | 514/63 |
| 2008/0118640 A1 * | 5/2008 | Kalkanoglu et al. ......... | 427/186 |

OTHER PUBLICATIONS

Office action from Mexican patent application No. MX/a/2011/000158 dated May 30, 2013.
Second office action from Mexico patent application No. MX/a/2010/001268 dated Jan. 23, 2014.

* cited by examiner

*Primary Examiner* — Nathan Van Sell
(74) *Attorney, Agent, or Firm* — Baker & McKenzie LLP

(57) ABSTRACT

The disclosed principles provide a roofing product and related methods of manufacturing having antimicrobial properties. The antimicrobial properties are provided by an antimicrobial delivery system including antimicrobial materials compounded, e.g., mixed together and melted, with polymeric materials. The antimicrobial delivery system is applied to roof covering material during the production process. The roof covering material may be sheets, shingles, panels, or roll stock.

12 Claims, No Drawings

ANTIMICROBIAL DELIVERY SYSTEM FOR ROOF COVERINGS

TECHNICAL FIELD

This invention relates to roof coverings, and more specifically to providing an antimicrobial material to roof coverings.

BACKGROUND

Roofing granules, both natural and artificially colored granules, are extensively used in roll roofing and asphalt shingle compositions. The roofing granules are embedded in the asphalt coating on the surface of the asphalt-impregnated base material, the granules thus forming a coating that provides an adherent, weather-resistant exterior roofing surface. These shingles sometimes develop dark blotches or streaks on the surfaces of asphalt shingles, especially in warmer humid climates, because of the growth of algae and other microorganisms. Algae typically causes stains on shingles, which not only hurts aesthetics, but can also dislodge granules causing damage to shingles. In addition, algae holds water which can damage roofs, shortening roof life, and causes leaking Some methods used to remedy such roof discoloration can dislodge protective granules such as with power washing or bleaching and can be followed with short-lived, periodic topical treatments using organic algaecides or inorganic metal salt solutions. Copper or zinc metal ridge flashing can be added as a pre- or post-installation step to the roof that can act as a longer term inhibitor. Zinc and copper flashing have been replaced over the years with aluminum and galvanized steel due to cost. Antimicrobial roofing systems have been used for many years and have employed various antimicrobial substances to deter naturally occurring growths on the roofing system. A widely used antimicrobial substance is copper. A common method currently in use provides special granules containing copper that are mixed with the colored granules on roof coverings during manufacturing, from about 1% to about 15% with about 8% to about 10% by weight the most common concentration.

The copper granules are typically produced by the manufacturers of color granules (for example, 3M and ISP Minerals) for use on roof coverings that use colored granules on the exposed surface of the roofing product. The copper granules are made up of a solid rock base material and coated with a copper containing coating that is kiln fired on the base rock. The copper granules usually come in black, white or gray colors. The copper granules are then mixed with other colored granules and applied to the roof covering product during the product manufacturing process. The copper-containing granules leach copper ions during the service life of the algae-resistant shingle to inhibit algae growth on the shingle surface even when the shingle surface is exposed to substantial moisture. The algae inhibitor has more localized coverage on the shingle as opposed to coming from a remote strip.

While algae-resistant shingles using copper-containing granules have been well known for many years, they are costly due to the additional cost of producing the copper-containing granules. Therefore, what is needed is an improved roofing product and method for providing resistance to naturally occurring growths on roofing systems that cause discoloration and/or deterioration of granule covered roof coverings including asphalt shingles.

SUMMARY

Embodiments in accordance with the disclosed principles provide an antimicrobial delivery system, which may be used for a roof covering or product. In one embodiment, an antimicrobial delivery system may comprise a polymer carrier. In addition, the system may comprise an antimicrobial material compounded with the polymer carrier and comprising a metal or metal compound. In such a system, degradation of the polymer carrier due to natural weathering releases the antimicrobial material over the period of degradation.

In another aspect, a sheet roofing product including a bituminous base and algae-resistant roofing granules is provided. In one embodiment, the roofing product includes base particles comprising an inert mineral adhered to the bituminous base. In addition, the roofing product may comprise an antimicrobial delivery system fused to the bituminous base at an interface where the base particles adhere to the bituminous base. In such embodiments, the antimicrobial delivery system comprises a polymer carrier compounded with an antimicrobial material comprising a metal or a metal compound, wherein degradation of the polymer carrier due to natural weathering releases the antimicrobial material over the period of degradation.

In yet another aspect, methods of manufacturing a roof covering are provided. In one embodiment, such a method may comprise providing a bituminous-based roofing sheet product. In addition, an exemplary method may provide for embedding a base particle comprising an inert mineral in an exterior surface of the sheet product. Additionally, the method may include fusing an antimicrobial delivery system to the sheet product at an interface where the base particles adhered to the sheet product. In such embodiments, the antimicrobial delivery system may comprise a polymer carrier compounded with an antimicrobial material comprising a metal or metal compound, wherein degradation of the polymer carrier due to natural weathering releases the antimicrobial material over the period of degradation.

DETAILED DESCRIPTION

The disclosed principles provide a roofing product and related methods of manufacturing having antimicrobial properties. The antimicrobial properties are provided by an antimicrobial delivery system including antimicrobial materials compounded with polymeric materials. Depending on resin choice, other possible interactions are not ruled out between the antimicrobial agent and carrier resin to give rise to an interfacial effect. Additives to enhance an interfacial effect, such as complexation agents or branch copolymers, are also potentially combined. The carrier resin is functional or acted upon by the environment in a number of possible ways that determine the release rate. Generally, the carrier component is acted upon by mechanism not limited to oxidative chain scission, ultraviolet chain scission, reverse Diels Alder reaction, esterases or other biochemical means, hydrolysis, and so on. UV additives could be used but are often cost negative and can instead be replaced in accordance with the disclosed principles by, for example, adjusting the amount of polymer, lowering particle size, and adding more AMS.

Other material property selection factors include brittleness that intermesh with process wear taking advantage of friability or some other planned physical degradation. Also adhesion to a shingle or asphalt surface is an important selection parameter. The antimicrobial delivery system is applied to roof covering material during the production process. The roof covering material may be sheets, shingles, or roll stock. The solution may be added to each of these during manufacturing as a granule or strip, after manufacture as a sticky granule, coating containing AMS particles, strip flashing, or overlain as a fibrous mat as a temporary poultice on a roof In some embodiments, the antimicrobial delivery system includes one or more antimicrobial materials at levels sufficient to retard or inhibit the growth of natural occurring roof staining organisms. Such organisms are typically made up from the cyanobacteria or blue-green algae classified organisms. The antimicrobial materials are released over time by the degradation of the polymeric carrier due to natural weathering factors. Thus, the disclosed principles take control of a negative property (i.e., degradation) of certain polymers in exterior conditions, and manipulate those characteristics to mete out antimicrobial agent over a selected period of time. In some embodiments, release of the antimicrobial material may be over a period of ten years, but other formulations are also possible.

The antimicrobial delivery system is dispersed on a roof covering product during the roofing product manufacturing process. During the roofing product manufacturing process, the roofing material is embedded with granules. As is well known, the granules (typically crushed stone such as Andesite, commonly known as trap rock, or nepheline syenite) serve to protect the roofing material from ultraviolet degradation. These granules can also be selected to decorate the resultant shingle by providing color or color patterns that enrich the roof covering appearance. The antimicrobial delivery system may be applied to the shingle base product with the granules or before the granule application in the manufacturing process. In a preferred embodiment, the antimicrobial delivery system fuses or sticks to a hot asphaltic coating at the interface where the granules adhere to the asphalt coating, and are dispersed across the shingle exterior surface among the granules. By dispersing the delivery system (i.e., antimicrobial material and polymer carrier) among the granules, for example at 5% or 10% loading on the shingle, the delivery system may be generally masked from view when viewing the shingle at a distance. The antimicrobial delivery system may also be used with non-asphaltic coatings that are, for example, water- or solvent-based, where the antimicrobial delivery system is applied with or before the granules and before the coating is cooled or cured. Other exemplary applications also include use on stone coated steel, as well as decorative imitation stone for exterior walls. In these embodiments, although a spray may be employed, granules or other stone-like delivery systems may be more beneficial and blend in nicely with the inert materials. Furthermore, the disclosed principles may also work on cement-based roof tile or siding. Of course, other applications not listed here are also possible, and no limitation to any examples disclosed herein is intended or should be inferred.

The antimicrobial delivery system includes one or more polymeric compounds for delivering the antimicrobial material to the roofing product. The polymeric compounds can be homopolymers or copolymers that are linear or branched. Copolymers may be random, alternating or block; and either class may have superstructure such as comb or dendritic characteristics. Examples of polymeric compounds can include acrylic copolymers, polyesters, polyamides, epoxies, nonacid-containing polyolefins, polyolefin alloys, polypropylene, acid-containing polyolefins, polyvinyl chloride, polyester block amide, ethylene-chlorotrifluorethylene, nylons, and polyvinylidene fluoride. However, the specific polymer material is selected by property of outdoor durability by weathering or biodegradability, compatibility with antimicrobial agent, physical and process properties. In some embodiments, the carrier could also be thermoplastic or thermoset. Preferably, the polymeric compounds are selected from high density, low density, and linear low density polyethylene; polypropylene; low and high impact polystyrene, PVC, ABS, polyamide, polyester, polycarbonate, SBS, SBR, SEBC and acrylic. In a presently preferred embodiment, the polymeric compound is polypropylene. In another presently preferred embodiment, the polymeric compounds is polystyrene. However, it should be noted that these examples are not meant to reduce the scope of available material choices. The polymeric compound is preferably cut or ground to a desired particle size. In some embodiments, the particle size of the polymeric compound ranges from about 0.01 mm to about 10 mm. In a specific embodiment, the particle size of the polymeric compound ranges from about 0.8 mm to about 2.5 mm. However, in accordance with the disclosed principles, there should be no limit to particle size. For example, in an embodiment where the polymeric carrier and antimicrobial material are provided in a spray coating, the spray particle in a coating could be 85 nanometers.

The antimicrobial material of the antimicrobial delivery system may be one or more metal oxides, metal powders, powders of metal alloys, copper compounds, metal sulfides, metal salts, organo-metallic compounds, known antimicrobial products, and combinations thereof. Examples of metal powders include, but are not limited to, zinc, copper, lead, tin, bronze, nickel, cadmium, or silver. Examples of metal compounds include, but are not limited to, zinc borate or barium metaborate. In a preferred embodiment, the antimicrobial material is cuprous oxide. In an alternate embodiment, the antimicrobial material is a mixture of cuprous oxide and zinc borate. Any antimicrobial material selected should be able to withstand the process of making the polymeric compound, the roofing product, and should have a desired durability once applied to the roofing product. In some cases, such as with cuprous oxide, the compound should be kept sealed from moisture or used within a short time period, i.e., before converting into copper oxide. But in almost all other known cases, the antimicrobial material does not require any special handling or other processing before being compounded with the polymer.

The antimicrobial material is compounded with the polymeric compound to provide the antimicrobial delivery system. The antimicrobial delivery system is processed to have a particle size range between about 0.01 mm to about 10 mm. In a specific embodiment, the particle size of the antimicrobial delivery system ranges from about 0.8 mm to about 2.5 mm. It should be noted that aesthetics (e.g., blending with shingle granules) can govern particle size, however, so too can the application vehicle (e.g., granules vs. a spray coating). The compounding may be done through any of the typical plastic compounding processes including, but not limited to, extrusion, injection molding, or compression molding. The concentration of the antimicrobial material in the antimicrobial delivery system ranges from about 1% by wt to about 90% by wt. In each particular embodiment, however, the concentration of the antimicrobial material in the antimicrobial delivery system compared to the polymer carrier will vary based on the delivery vehicle chosen. Thus, the concentration selected is a durability control parameter—the more polymer, the longer lasting, and vice versa.

The antimicrobial delivery system can also include other components, such as curing agents or hardeners, extenders, and additives such as flow modifiers, and the like. In some embodiments, the additives may promote the release of the antimicrobial material or delay the release of the antimicrobial material or improve in the antimicrobial delivery process. Example of possible additives include compatibilizers, UV additives, antioxidants and other thermoplastics known to those skilled in the art. However, like concentration and particle sizes, the use or non-use of additives, and which additives if any, may be dependent on the application of the disclosed principles, as well as the selection of the polymeric carrier parameters.

The antimicrobial delivery system may be applied to the roof covering product by mixing it with the colored granules or by applying the antimicrobial delivery system before the colored granules are applied. The methods or techniques for applying the granule material are common knowledge in the industry. In a preferred embodiment, the weight ratio of the antimicrobial delivery system to colored granules ranges from about 0.01:99.99 to about 20:80. In a specific exemplary embodiment, a 10% by weight cuprous oxide has been used in a polymer loaded at 3.3% by weight with roofing granules. This has been shown to be approximately equal to a 10% loading of the currently used copper based algae resistant granule with roofing granules. The amount of the antimicrobial material delivery system in the roofing system can be adjusted depending on, but not limited to, the intended use of the roofing products manufactured using the antimicrobial delivery system, the expected environmental conditions at the site where the roofing products including the antimicrobial delivery system are to be installed, the proportion of antimicrobial material in the antimicrobial material delivery system, the proportion of the antimicrobial material delivery system to the conventional roofing granules employed in the roofing product, etc.

The antimicrobial delivery system can be employed in the manufacture of algae-resistant roofing products, such as algae-resistant asphalt shingles, using conventional roofing production processes. Roofing products are sheet goods that typically include a non-woven base or scrim formed of a fibrous material, such as a glass fiber scrim or mat. The base is coated with one or more layers of a material such as asphalt to provide water and weather resistance to the roofing product. One side of the roofing product is typically coated with mineral granules to provide durability, reflect heat and solar radiation, and to protect the bituminous binder from environmental degradation. In a preferred embodiment, the antimicrobial delivery system can be mixed with conventional roofing granules, and the granule mixture can be embedded in the surface of such roofing products using conventional methods. In an alternate embodiment, the antimicrobial delivery system can be substituted for conventional roofing granules in the manufacture of bituminous roofing products to provide those roofing products with algae-resistance.

Roofing products are typically manufactured in continuous processes where a continuous substrate sheet of a fibrous material such as a continuous felt sheet or glass fiber mat is immersed in a bath of hot, fluid bituminous coating material so that the bituminous material saturates the substrate sheet and coats at least one side of the substrate. The reverse side of the substrate sheet can be coated with an anti-stick material such as a suitable mineral powder or a fine sand. Roofing granules are then distributed over selected portions of the top of the sheet, and the bituminous material serves as an adhesive to bind the roofing granules to the sheet when the bituminous material has cooled. The sheet can then be cut into conventional shingle sizes and shapes (such as one foot by three feet rectangles), slots can be cut in the shingles to provide a plurality of "tabs" for ease of installation, additional bituminous adhesive can be applied in strategic locations and covered with release paper to provide for securing successive courses of shingles during roof installation, and the finished shingles can be packaged. More complex methods of shingle construction can also be employed, such as building up multiple layers of sheet in selected portions of the shingle to provide an enhanced visual appearance, or to simulate other types of roofing products.

In some embodiments, the roofing material is a bituminous material derived from a petroleum processing by-product such as pitch, "straight-run" bitumen, or "blown" bitumen. The bituminous material can be modified with extender materials such as oils, petroleum extracts, and/or petroleum residues. The bituminous material can include various modifying ingredients such as polymeric materials, such as SBS (styrene-butadiene-styrene), block copolymers, resins, oils, flame-retardant materials, oils, stabilizing materials, anti-static compounds, and the like. The bituminous material may also include a suitable filler, such as calcium carbonate, talc, carbon black, stone dust, or fly ash.

EXAMPLES

Embodiments of antimicrobial delivery systems are shown below:

TABLE 1

| Example | Polypropylene, wt % | Polystyrene, wt % | Cuprous Oxide, wt % | Zinc Borate, wt % |
|---|---|---|---|---|
| 1 | 89.9 | 0 | 10.1 | 0 |
| 2 | 0 | 89.9 | 10.1 | 0 |
| 3 | 0 | 79.8 | 10.1 | 10.1 |
| 4 | 50 | 0 | 25 | 25 |
| 5 | 50 | 0 | 50 | 0 |

The above antimicrobial delivery systems were produced using plastic extrusion and pelletizing equipment (in this specific case, a twin screw extruder was employed), both of which are commonly used in plastic compounding. The extruder used in this example metered the polymer and antimicrobial materials at the desired percentages into the extruder where they were mixed, melted, and extruded. The pellets ranged in size between about 1.0 mm and about 2.5 mm. Examples 1, 2, and 3 would be used at ⅓ the weight of the loading used for the currently used rock based copper granules (e.g., 3M LR7000 or LR7070 and ISP A901 or A902) to deliver the equivalent amount of cuprous oxide to the roof covering. The ratio for Examples 4 is ⅛ the copper granule loading. The ratio for Examples 5 is 1/16 the copper granule loading. Again, these measurements are calculated by weight of copper in polymeric carrier vs. weight of copper in the rock-based granules. The amounts used in the disclosed examples are less because the antimicrobial material is encapsulated by the polymer and not with the rock granule. The plastic density of the polymer is much less than that of the rock base used on current 3M or ISP copper granules. Accordingly, in advantageous embodiments, the resulting lower loading amount would require less copper, and therefore decreases manufacturing costs.

Other exemplary loading formulations employ cuprous oxide at 20%, 30% and 50% loading, and zinc metal powder at 25% and 50% loading, in the polymer. Moreover, the extruded pellet size may be reduced, e.g., by grinding the extruded pellet to −16 mesh and +20 mesh US screen size. This creates more surface area of the AR polymer granules in the blend, and increases the number of points of AR activity. Per the US Standard sieve size opening, the particle size would be between 0.85 and 1.00 mm in such examples.

While various embodiments of the disclosed principles have been described above, it should be understood that they have been presented by way of example only, and not limitation. Thus, the breadth and scope of the invention(s) should not be limited by any of the above-described exemplary embodiments, but should be defined only in accordance with any claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed:

1. An algae-resistant sheet roofing product including a bituminous base and roofing granules, the sheet roofing product comprising:
   base particles comprising an inert mineral directly adhered to the bituminous base; and an antimicrobial delivery system fused to the bituminous base at an interface where the base particles adhere to the bituminous base, the antimicrobial delivery system comprising a polymer carrier compounded with an antimicrobial material comprising particles of a metal or a metal compound;
   wherein the polymer carrier independently encapsulates the particles of the antimicrobial material such that degradation of the polymer carrier due to natural weathering releases the antimicrobial material over the period of degradation;
   wherein the polymer carrier does not encapsulate the base particles;
   wherein the polymer carrier is selected from the group consisting of nylons, polyester block amide, ethylene-chlorotrifluoroethylene, acrylonitrile butadiene styrene, and styrene ethylene butadiene copolymer;
   wherein the antimicrobial delivery system is configured to be fused to the sheet roofing product via a hot asphalt coating proximate to an interface where the base particles adhere to the asphalt coating,
   wherein the antimicrobial material comprises cuprous oxide and zinc borate; and
   wherein the weight ratio of the polymer carrier to cuprous oxide to zinc borate is about 80:10:10.

2. The roofing product of claim 1, wherein the antimicrobial delivery system has a diameter ranging from about 0.5 to about 2.5 mm.

3. The roofing product of claim 1, further comprising an additive compounded with the polymeric carrier and the antimicrobial material, the additive affecting the release of the antimicrobial material.

4. The roofing product of claim 3, wherein the additive is a UV additive or a compatibilizer.

5. The roofing product of claim 1, wherein the weight ratio of the antimicrobial delivery system to inert base particles ranges from about 10:90 to about 90:10.

6. A method of manufacturing a roof covering, the method comprising: providing a bituminous-based roofing sheet product;
   directly adhering base particles comprising an inert mineral to an exterior surface of the sheet product; and
   fusing an antimicrobial delivery system to the sheet product at an interface where the base particles adhere to the sheet product, the antimicrobial delivery system comprising a polymer carrier compounded with an antimicrobial material comprising particles of a metal or a metal compound;
   independently encapsulating the particles of the antimicrobial material such that degradation of the polymer carrier due to natural weathering releases the antimicrobial material over the period of degradation;
   wherein the polymer carrier does not encapsulate the base particles;
   wherein the polymer carrier is selected from the group consisting of nylons, polyester block amide, ethylene-chlorotrifluoroethylene, acrylonitrile butadiene styrene, and styrene ethylene butadiene copolymer;
   wherein the antimicrobial delivery system is fused to the roofing sheet product via a hot asphalt coating proximate to an interface where the base particles adhere to the asphalt coating,
   wherein the antimicrobial material comprises cuprous oxide and zinc borate; and
   wherein the weight ratio of the polymer carrier to cuprous oxide to zinc borate is about 80:10:10.

7. The method of claim 6, wherein the antimicrobial delivery system has a diameter ranging from about 0.5 to about 2.5 mm.

8. The method of claim 6, further comprising an additive compounded with the polymeric carrier and the antimicrobial material, the additive affecting the release of the antimicrobial material.

9. An algae-resistant sheet roofing product having an exterior surface, the sheet roofing product comprising:
   a bituminous base;
   roofing granules comprising an inert mineral directly adhered to the bituminous base forming an interface where the granules adhere to the base; and
   an antimicrobial delivery system dispersed on the sheet roofing product, the antimicrobial delivery system comprising:

a polymer carrier compounded with an antimicrobial material comprising particles of a metal or a metal compound, the polymer carrier independently encapsulating the particles of the antimicrobial material but not the base particles, wherein degradation of the polymer carrier due to natural weathering releases the antimicrobial material over the period of degradation, wherein the polymer carrier does not encapsulate the base particles;

wherein the polymer carrier is selected from the group consisting of nylons, polyester block amide, ethylene-chlorotrifluoroethylene, acrylonitrile butadiene styrene, and styrene ethylene butadiene copolymer;

wherein the antimicrobial delivery system is dispersed across the exterior surface of the sheet roofing product and is configured to be fused to the sheet roofing product via a hot asphalt coating proximate to an interface where the granules adhere to the asphalt coating, wherein the antimicrobial material comprises cuprous oxide and zinc borate; and wherein the weight ratio of the polymer carrier to cuprous oxide to zinc borate is about 80:10:10.

10. A method of manufacturing a roof covering, the method comprising:

directly adhering roofing granules to an exterior surface of a bituminous-based roofing sheet product, the roofing granules comprising an inert mineral;

fusing an antimicrobial delivery system to the sheet product at an interface where the roofing granules adhere to the sheet product, the antimicrobial delivery system comprising a polymer carrier compounded with an antimicrobial material comprising particles of a metal or a metal compound;

wherein the polymer carrier independently encapsulates the particles of the antimicrobial material such that degradation of the polymer carrier due to natural weathering releases the antimicrobial material over the period of degradation;

wherein the polymer carrier is selected from the group consisting of nylons, polyester block amide, ethylene-chlorotrifluoroethylene, acrylonitrile butadiene styrene, and styrene ethylene butadiene copolymer; and fusing the antimicrobial delivery system to the roofing sheet product via a hot asphalt coating proximate to an interface where the roofing granules adhere to the asphalt coating;

wherein the antimicrobial material comprises cuprous oxide and zinc borate; and wherein the weight ratio of the polymer carrier to cuprous oxide to zinc borate is about 80:10:10.

11. An algae-resistant sheet roofing product including a bituminous base and roofing granules, the sheet roofing product comprising:

base particles comprising an inert mineral directly adhered to the bituminous base; and an antimicrobial delivery system fused to the bituminous base at an interface where the base particles adhere to the bituminous base, the antimicrobial delivery system comprising a polymer carrier compounded with an antimicrobial material comprising particles of a metal or a metal compound;

wherein the polymer carrier independently encapsulates the particles of the antimicrobial material such that degradation of the polymer carrier due to natural weathering releases the antimicrobial material over the period of degradation;

wherein the polymer carrier does not encapsulate the base particles;

wherein the polymer carrier is selected from the group consisting of nylon, polyester block amide, ethylene-chlorotrifluoroethylene, acrylonitrile butadiene styrene, and styrene ethylene butadiene copolymer;

wherein the antimicrobial delivery system is configured to be fused to the sheet roofing product via a hot asphalt coating proximate to an interface where the base particles adhere to the asphalt coating, and wherein the antimicrobial delivery system is sized to have −16 mesh.

12. An algae-resistant sheet roofing product including a bituminous base and roofing granules, the sheet roofing product comprising:

base particles comprising an inert mineral directly adhered to the bituminous base; and an antimicrobial delivery system fused to the bituminous base at an interface where the base particles adhere to the bituminous base, the antimicrobial delivery system comprising a polymer carrier compounded with an antimicrobial material comprising particles of a metal or a metal compound;

wherein the polymer carrier independently encapsulates the particles of the antimicrobial material such that degradation of the polymer carrier due to natural weathering releases the antimicrobial material over the period of degradation;

wherein the polymer carrier does not encapsulate the base particles;

wherein the polymer carrier is selected from the group consisting of nylon, polyester block amide, ethylene-chlorotrifluoroethylene, acrylonitrile butadiene styrene, and styrene ethylene butadiene copolymer;

wherein the antimicrobial delivery system is configured to be fused to the sheet roofing product via a hot asphalt coating proximate to an interface where the base particles adhere to the asphalt coating, and wherein the antimicrobial delivery system is sized to have +20 mesh.

* * * * *